United States Patent [19]
Deitrich

[11] Patent Number: 5,482,046
[45] Date of Patent: Jan. 9, 1996

[54] ACOUSTIC POWER CONTROL TECHNIQUE

[75] Inventor: Thomas L. Deitrich, Durham, N.C.

[73] Assignee: General Electric Company, Milwaukee, Wis.

[21] Appl. No.: 344,245

[22] Filed: Nov. 23, 1994

[51] Int. Cl.⁶ ....................................................... A61B 8/00
[52] U.S. Cl. ....................................................... 128/662.02
[58] Field of Search .......................... 128/660.02, 660.03, 128/660.04, 661.08, 662.02; 73/619, 620, 627, 628

[56] References Cited

U.S. PATENT DOCUMENTS 5,233,994  8/1993  Shmulewitz ........................ 128/661.08

Primary Examiner—George Manuel
Attorney, Agent, or Firm—B. Joan Haushalter; John H. Pilarski

[57] ABSTRACT

An acoustic power control technique computes relevant system transmit parameters in real-time by optimally combining a current system imaging configuration with an empirically derived measurement database. The database contains measurement information that is used by the acoustic power control technique to determine optimal transmit parameters for a given imaging situation. The optimal parameters are determined by adjusting the measured database parameters through the use of the current scanning parameters to maximize system performance. Utilizing system constraints, the acoustic power control technique computes the optimal transmit parameters to maximize system performance.

8 Claims, 1 Drawing Sheet

ACOUSTIC POWER CONTROL TECHNIQUE

TECHNICAL FIELD

The present invention relates to ultrasound imaging and, more particularly, to an acoustic power control technique for ultrasound imaging systems.

BACKGROUND ART

Ultrasound imaging systems generate ultrasonic echoes from deliberately launched diagnostic sound waves into tissue. The ultrasonic echoes are attenuated in proportion to the distance that the sound waves must travel to reach the reflector, plus the distance that the resulting echoes must travel back to reach the receiver. The ultrasound echoes are displayed on a screen, providing medical information for the operator.

All diagnostic ultrasonic imaging systems employ some type of acoustic power control. In general, the control of acoustic output levels are based on fixed pre-determined schemes. There are a number different parameters that directly or indirectly control the acoustic output power levels of an diagnostic ultrasonic imaging system. Numerous systems constraints affect control of the acoustic output power levels, including hardware limitations, transducer temperature limitations, and regulatory allowable dose limits. Since the control of acoustic output levels are based on fixed predetermined schemes, and numerous constraints exist, acoustic power control poses a difficult problem in diagnostic ultrasonic imaging systems.

It would be desirable then to have an acoustic power control technique which overcomes the problems associated with the prior art. The invention discussed here allows optimal dose limits to be achieved in real-time.

SUMMARY OF THE INVENTION

The present invention provides an acoustic power control technique capable of computing relevant system transmit parameters. The acoustic power control technique of the present invention utilizes a real time technique to dynamically adjust the transmit parameters of the system to optimize the acoustic power levels within imaging situation dependent constraints.

In accordance with one aspect of the present invention, an acoustic power control technique computes relevant system transmit parameters by optimally combining a current system imaging configuration with an empirically derived measurement database. The database contains measurement information that is used by the acoustic power control technique to determine optimal transmit parameters for a given imaging situation. The optimal parameters are determined by adjusting the measured database parameters through the use of the current scanning parameters to maximize system performance. Utilizing system constraints, the acoustic power control technique computes the optimal transmit parameters to maximize system performance.

Accordingly, it is an object of the present invention to provide an acoustic power control technique for diagnostic ultrasonic imaging systems. It is another object of the present invention to provide such an acoustic power control technique which utilizes a real time technique to dynamically adjust the transmit parameters of the system to optimize the acoustic power levels within imaging situation dependent constraints.

Other objects and advantages of the invention will be apparent from the following description, the accompanying drawings and the appended claims.

DETAILED DESCRIPTION OF THE PREFERRED EMBODIMENTS

Figure 1:
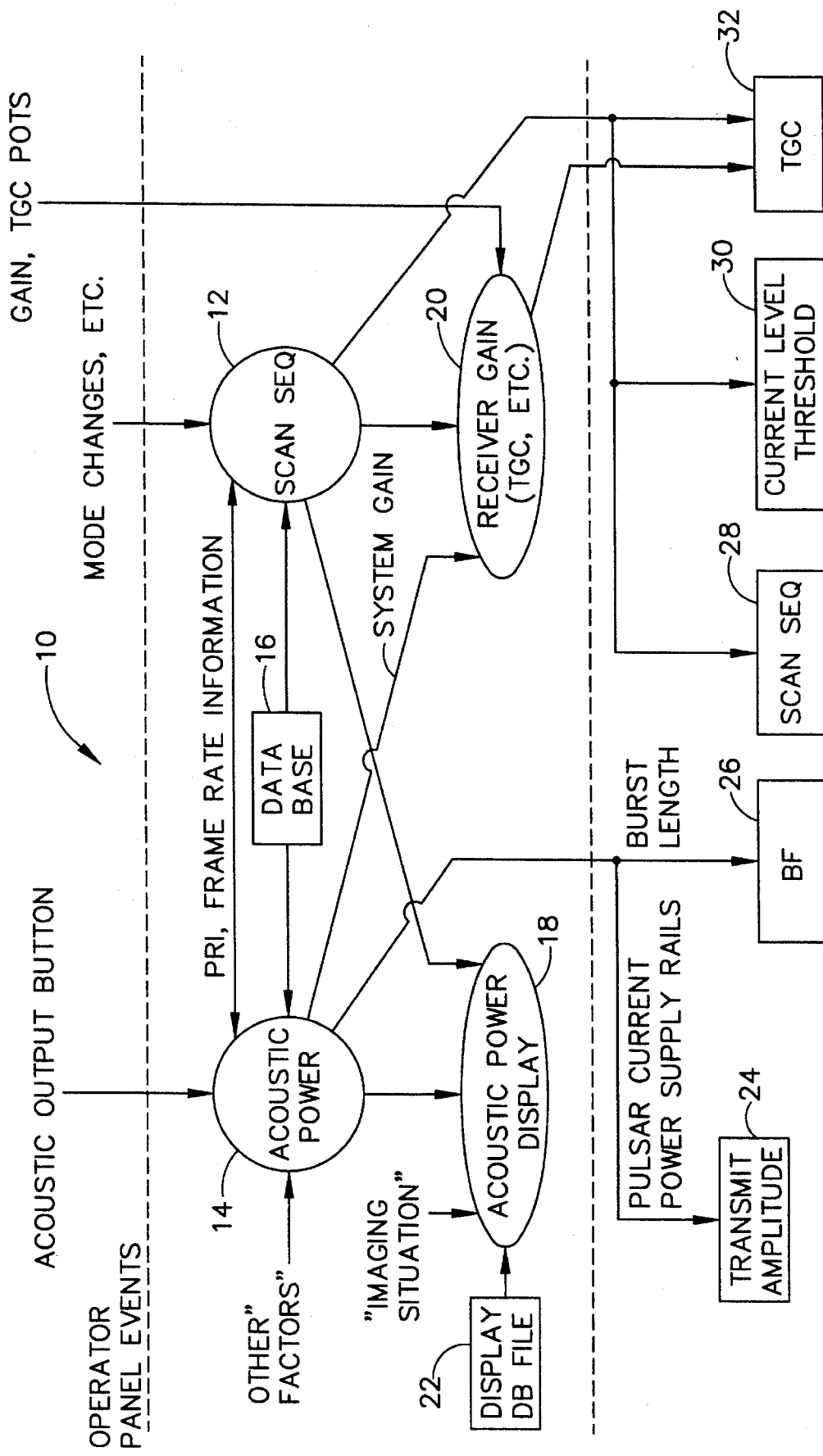
FIG. 1 illustrates a control flow block diagram of an acoustic power management technique structure in accordance with the present invention.

The present invention provides for an acoustic power control technique which utilizes a real time technique. The acoustic power control technique of the present invention dynamically adjusts the transmit parameters of the system to optimize the acoustic power levels within imaging situation dependent constraints.

The acoustic power control technique of the present invention computes relevant system transmit parameters by optimally combining the current system imaging configuration with an empirically derived measurement database. The technique considers a number of constraints to optimally compute the transmit parameters, including (1) time averaged hardware capability, or average power output; (2) single event hardware capability, or peak power output; (3) transducer elemental impedance; (4) transducer thermal dissipation capability; (5) applicable regulatory output limits, such as FDA dose limits; (6) system operating modes or geometries; (7) transducer and operating mode transmit frequency; (8) operating mode transmit locations; (9) operator acoustic power output control selection; and (10) selected exam category.

Utilizing these inputs, the acoustic power control technique of the present invention computes optimal transmit parameters to maximize system performance. A number of parameters are produced by the acoustic power control technique, including transmit amplitude, transmit burst length, transmit pulse repetition rate, transmit vector density, transmit aperture size, transmit aperture phase center location, high voltage supply control parameters, receiver gain adjustment amount, high voltage power supply safety monitor threshold, and actual output dose parameters for output display index conversion.

Referring now to FIG. 1, there is illustrated a top level block diagram of the acoustic power control technique according to the present invention. The control method 10 relies on an empirically derived measurement database. This database contains measurement information that is used by the acoustic power control technique 10 to determine optimal transmit parameters for a given imaging situation. The optimal parameters are determined by adjusting the measured database parameters through the use of the actual scanning parameters to maximize system performance.

The acoustic power control technique database is a multidimensional data structure that is composed of measured parameters. The major dimensions of the database structure comprise a transducer, transmit frequency, which, although both are operator selectable within factory specified limits, a database may be maintained containing all the measured data for all transducers and frequencies. Major dimensions of the database structure also comprise exam category selections, such as general abdominal, small parts, cardiology, OB/GYN, vascular, and neonatal. Although all of these are user selected, the system contains a database of measured data values for all exam categories. Major dimensions of the database structure further comprise system imaging modes, including brightness mode (B), motion mode (M), pulse echo mode (PE), continuous wave mode (CW), color flow mode (CF), and color flow motion mode (CFM). Finally, the database structure comprises transmit focal range selections, which are user selectable. Again, the system contains a database of measured values for all modes and transmit locations.

Each unique cell in the database structure, identified by a combination of the above-mentioned dimensions of the database, contains a number of measurement based records. These records are used to adjust current operating parameters to maximize system performance. The records contained in the database comprise measured output total acoustic power (mW); measured spatial peak time average intensity (mW/cm$^2$); transmit aperture size (elements); transmit electrical current levels (Amps); integral of transmit apodization function (unitless); measured pulse intensity integral (v$^2$-microseconds); transmit burst length (cycles); firing pulse repetition interval (microseconds); number of transmit vectors per frame (unitless); interleaving amount of transmit vectors (unitless); transmit vector packet size (unitless); transmit vector spacing (radians or mm); mixed mode duty cycle (unitless); and peak rarefactional pressure (MPa).

During normal operation of the system, controls on the operator panel will be manipulated to provide diagnostic information relevant to the case at hand. After each modification of the state to the control panel by the operator, the ultrasound system will receive inputs describing the present imaging situation. These inputs are acted upon by an software control structure to optimize the acoustic output.

In particular, a scan sequencer routine, denoted as block 12 in FIG. 1, collects and processes mode and operator control information to produce frame rate and PRI data. This data is then combined with operator selected acoustic output levels and measurement database information in the acoustic power control routine, denoted as block 14 in FIG. 1. Block 16 is a measurement derived database file that is utilized by the scan sequencer 12 routine to compute time constraint information, and by the acoustic power control routine 14 to optimally compute transmit parameters, such as transmit amplitude, transmit power supply control parameters and transmit burst length. The acoustic power control routine 14 also provides accurate estimates of physical output data that is used by the acoustic power display calculation routine, shown in block 18. The acoustic output display routine 18 computes the output display indices (i.e. MI and TI) in accordance with the relevant regulations. Additional measurement data used in the calculation of the display indices is supplied to the acoustic power display calculation routine by the display database file shown in block 22 of the diagram. The acoustic power display calculation routine 18 also receives additional information, such as the selected transducer geometry, that is employed in the index calculations; this information is denoted as "other factors" in the figure.

A modification in the acoustic output levels computed by the acoustic power control routine 14 may require a modification in the receiver gain level to be enacted to prevent a change in the overall brightness of the image. If this modification in the receiver gain level is required, system gain level information is sent to the receiver gain level routine shown in block 20. The receiver gain level routine 20 combines the operator selected inputs with the outputs of the acoustic with the outputs of the acoustic power control routine to compute modified gain levels which will be sent to the system hardware for implementation.

After all of the required changes in the programming of the hardware due to the operator inputs are computed, these data are delivered to the hardware platform. This task is accomplished by blocks 24 through 32 in FIG. 1. Block 24, the transmit amplitude delivery routine, receives transmit amplitude and power supply control parameters from the acoustic power control routine 14. This data is then delivered into the relevant hardware registers. A beam former (BF) routine, shown in block 26, utilizes the burst length information received from the acoustic power control routine 14 to compute and deliver relevant beamforming parameters to the hardware registers. Scan sequence vector firing lists and timing information are delivered to the hardware by the scan sequence delivery routine shown in block 28. Hardware and patient protection is provided by electrical current monitors hardware which is programmed in block 30, the current level threshold routine. The current level threshold routine 30 combines scan sequencer 12 and acoustic power control routine 14 data to determine hardware shutdown levels in various failure modes. The TGC routine, shown in block 32, delivers update receive gain information to control image appearance and signal to noise levels.

It will be obvious to those skilled in the art that the concept of the present invention can be implemented in a variety ways, including hardware and software implementations. Although one such implementation is described herein, it is to be understood that this is for purposes of description only, and is not to be considered as limiting the scope of the invention.

In accordance with one implementation of the acoustic control technique of the present invention, an acoustic power management scheme (control, estimation, and display) is described for an ultrasound system. The scheme includes acoustic and electrical power control, as well as the calculation of inputs for acoustic power display indices. A general power management philosophy provides the operator with the capability to increase and decrease the acoustic output in system designated steps. Real-time display indices are exhibited to the operator to provide guidance on possible biological tissue effects created by the acoustic dose, i.e., inputs are provided to the output display calculations.

Laboratory developed databases, in conjunction with analytical expressions for control are used. The approach discussed herein decouples the scan sequence processing from acoustic power control, wherein a shared database is implemented to minimize data transfer between software functions.

It is noted here that there are some limitations in the power management implementations. The configuration according to the present invention makes use of piecewise linear approximations for power control. The method of the invention does not account for functional vector spacing, and the power control is not dependent on angle. These limitations are handled in a manner to insure conservative, yet diagnostic quality, system outputs and operator presented power output displays.

The present invention proposes a process used to develop inputs to existing FDA created display algorithms. The control and display of acoustic output is interdependent on many of the basic parameters of the system. The system is equipped with five levels of acoustic power output, adjustable using an acoustic output "button" located on an operator control panel. The highest output level corresponds to the FDA prescribed limit (Mechanical Index (MI) or Intensity at the spatial peak, time coverage, of the acoustic field ($I_{SPTA}$), depending on the transducer mode/depth of the situation), or the system electrical power limit, whichever is lower. When the system is "powered-up", or a new transducer or new patient selected, or a different exam category selected, a system default power setting will be enforced. The default setting is established based on the lowest output setting that provides a high quality diagnostic image. In general, this power setting is near the center of the full range of acoustic power output.

The power increment between the steps will not necessarily be uniform across all transducers/modes/depths. An increase in the acoustic output button will increase output power and display indices by some amount that will be conveyed to the user. Similarly, the operator will not be able to "dial-in" a specific display index. The control granularity of the output power button only allows the operator to increase or decrease the output power.

Continuing with FIG. 1, there is illustrated a top level control structure for the acoustic power management portion of the system software, in accordance with the present invention. The top portion (above upper dashed line) denotes operator induced events (e.g., gain changes, acoustic power increases, etc.). These external events trigger the execution of a software structure which is contained in the center portion of the drawing. Careful note should be made as to the interaction of the routines noted and the hierarchy of the routines, denoted by separate boxes in the drawing. For example, the acoustic power manager acts upon operator acoustic power requests directly, and feeds information to the display routine for output index processing. A change in acoustic power may result in a change in the receiver gain, which is controlled by the receiver gain/time gain compensation (TGC) routine, indicated by receiver gain block 20 in FIG. 1. This routine computes the gain levels that the hardware will use to process return echoes. However, the reverse is not true, as TGC gain change does not modify acoustic output. It should be noted that the interaction of the scan sequence parameter routine, implemented by the acoustic power routine, and the acoustic power routine (for computing vector firing recipes based on operator selected scanning situations), has been reduced. The only link illustrated between the two routines is a shared database, and basic mode information.

The acoustic power display parameter routine is a slave of the actual power manager routine. The exact output power is not "dialed-in" by the user; the acoustic power controls allow only an increasing or decreasing effect by a non-specific amount. The acoustic power manager sets the transmit parameters, such as amplitude, burst length, and power supply control information, and this information, along with other selected parameters, is passed to the display routine for processing. There are many other events that demand that the acoustic output display is updated beyond the acoustic output button and mode changes, which dependencies are represented as "other factors" in FIG. 1.

Following the flow down FIG. 1, the next section encountered comprises a series of subordinate software modules. These routines complete the calculations of the transmit parameters and send the appropriate information to the hardware. It is important to note the acoustic power output level is set almost entirely by the higher level software, between the dashed lines in the drawing. At the lower software levels, below the dashed lines in the drawing, the incoming parameters that modify acoustic output could be the result of any number of operator changes. The acoustic power management software is isolated to the higher level routines only. That is, acoustic output is "hidden" from the lower level software routines to the greatest extent possible.

This architecture allows the acoustic power routine to be unaffected by changes in software or hardware above or below the dashed lines.

Upon the selection of a new exam category, new transducer, new patient, and at "power-up", the system reverts back to the default power setting. This default setting is actually captured in a system "preset" database that is optimized to employ the lowest power to obtain a diagnostic image. Power levels are mapped into a percentage scale for ease of interpretation. The output power levels for each transducer are optimized for each scanning situation, which means that an 80% output level for transducer A is not necessarily equal to an 80% output level for transducer B. However, in both cases, the output display will indicate the appropriate mechanical/thermal indices to a predetermined accuracy. The operator may select various power levels, but cannot change the factory defaults contained in the system database. The system will always default back to the values in the database on a new exam type, patient, at "power-up", and upon the selection of a new transducer.

Continuing with FIG. 1, the major components of the acoustic power management section of the system are described. The database must obviously contain the acoustic power and intensity data and enough information to "retrace" the steps to its generation. Acoustic power output is dependent on a great many factors and as a result the size of the database becomes quite large. In a preferred embodiment of the present invention, the design for the database has the following dimensions: application, probe, frequency, mode, and transmit depth. At each location in this multidimensional database the following information is stored: total acoustic power, $W_0$, spatial peak intensity, $I_{SPTA}$, and a series of parameters relating to the output generation. These parameters are as follows: aperture size, pulsar current, PII, PRI, frame rate, interleave amount, packet size, minimum vector spacing, maximum electrical power available, and mixed mode power weighting factors.

The construction of this database is crucial to the ability to accurately and efficiently control and display output power. A quick estimate of database size can be computed as follows: six applications×eighteen probes×three frequencies×six modes×twelve depths×fourteen values per database location. The full database size, then, is approximately 8 MBytes, assuming sixteen bit values. The size of the database is alarming and definitely identifies the need to develop an automated measurement gathering system, in accordance with the present invention.

The scan sequencer will produce Pulse Repetition Intervals (PRI) for each of the vector types. These PRIs are computed based on depth, velocity scale, etc. as appropriate. Hence, the circularity problem of requiring the power levels to compute vector timing and vice versa are avoided by computing the PRI first and forcing the power to live within the PRI/timing constraints.

As will be understood by those skilled in the art, the active aperture size of a transducer also affects the acoustic output levels achieved with a particular transducer. The total power through the aperture is proportional to the size of the aperture, although the dependency of intensity on aperture size is related to the amount of focussing provided by the aperture.

A major factor in determining the amount of power present in any particular beam is the length and shape of the transmit pulse. For the purposes of power prediction, it is assumed that the pulses from all array channels are identical in shape. Transmit apodization modifies the amplitude of each channel pair. In terms of power and intensity, the integral of the pulse shape determines the power adjustment factor. The acoustic power routine, as discussed herein, receives as an input a transducer bandwidth estimate and computes the number of transmit cycles, based on the mode and appropriate pulse length determination, which is a linear fit of PII and burst length. The slope of the fit line, then, is experimentally determined. The convolution of these two factors provides an estimate of the pulse shape and when squared-integrated creates a Pulse Intensity Integral (PII). Both total acoustic power and temporal average intensity scale change with the change in PII.

A transmit shading or aperture weighting function can be used to shape the beam profile to reduce aperture edge effects by de-emphasizing the elements near the edge of the array. The weighting function affects the total power sent "through" the aperture into the media. The transmit shading function also modifies the distribution of the energy within the beam profile. The sum total of these effects on total acoustic power is fairly straight forward. That is, power scales with the processing gain/loss of the window function.

To this point in the power adjustment factor development, the order of the adjustments has not mattered, since of the operations are linear and applied to a single vector. After the application of multiple vector adjustors, the single vector amplitudes can be computed and used to determine the appropriate thermal indices and pulse current levels.

The spacing between vectors determines the amount of interaction between the vectors to increase the power and intensity. The vector spacing varies as a function of steering angle to maintain a constant delta sine theta spacing. To maintain relative simplicity in the acoustic power prediction, the variable vector spacing can be neglected and the power/intensity adjusted based on a linear shift with varying vector spacing.

The power and temporal average values for a particular scan sequence also depend on the packet size used for various vector types. This applies particularly well to Color Flow mode, and can be adapted to multiple focal zones in B-mode imaging as well, where the zone that has the largest amplitude is selected and used for each zone, with the number of zones equaling the packet size. Knowing all of these factors allows the power and intensity levels to be computed for the current imaging situation and also allows the pulser current levels to be computed that may achieve the predicted power levels.

At this point, the acoustic output levels must be computed for the entire frame. The adjustments to the power levels implemented to this point account for individual vectors and vector packets. It should be noted that the scan sequencer calculates the vector PRI(s), the acoustic frame rate, and the interleave amount (packet size is known by the scan sequencer as well as by other routines). All of these parameters are required in order to compute the number of vectors in a frame and the number of vectors of mode 'x' in the frame.

The interpretation of the number of vectors within a frame (for the entire frame or per mode) has a subtle point that must be considered when computing the total power and intensity for the image frame. The acoustic frame rates for B-mode and CF-mode may differ if the frame rate attempting to be maintained is very high. For example, in some scan sequences the CF window may be updated twice as often as the B-mode window is acoustically updated. When this type of situation occurs, the incoming frame rates passed to the acoustic power parameter routine, as discussed herein, should detect the difference in frame rates and compute the total frame power and intensity levels, based on the lowest common denominator of the frames.

An increase in acoustic output levels should (presumably) increase the strength of the return echoes. This increase in return signal levels would be perceived by the operator as an increase in brightness on the monitor, which is undesirable. In order to "normalize" the gain levels for the entire loop, a system gain adjustment can be applied to adjust the TGC/system gain values in accordance with any increase/decrease in acoustic output levels.

Furthermore, the amount of power produced by a system is intimately related to the shape (length, width, and height) of the transmit burst. Determination of transmit burst is dependent on inputs comprising mode, transmit depth, system/transducer bandwidth, range gate position/size, etc.; and outputs, comprising the number of transmit cycles to be used.

The acoustic power control technique documented herein computes the relevant system transmit parameters by optimally combining the current system imaging configuration with an empirically derived measurement database. The technique considers the following constraints to optimally compute the transmit parameters comprising: (1) time averaged hardware capability, or average power output; (2) single event hardware capability, or peak power output; (3) transducer elemental impedance; (4) transducer thermal dissipation capability; (5) applicable regulatory output limits, such as FDA dose limits; (6) system operating modes or geometries; (7) transducer or operating mode transmit frequency; (8) operating mode transmit locations; (9) operator acoustic power output control selection; and (10) selected exam category. Utilizing these inputs, the acoustic power control technique of the present invention computes optimal transmit parameters to maximize system performance.

The invention has been described in detail with particular reference to certain preferred embodiments thereof, but it will be understood that modifications and variations can be effected within the spirit and scope of the invention.

What is claimed is:

1. An acoustic power control method for optimizing acoustic power levels in an ultrasound imaging system having an operator control panel, the method comprising the steps of:

providing a measurement database containing measured database parameters;

optimally combining a current system imaging configuration with the measured database parameters to provide an optimal combination;

computing relevant system transmit parameters using the optimal combination to achieve optimization of transmit parameters;

using a scan sequencer to collect and process mode and operator control information to produce frame rate and pulse repetition intervals data; and adjusting the measured database parameters through the use of current scanning parameters to maximize system performance.

2. An acoustic power control method as claimed in claim 1 wherein the optimization of transmit parameters is computed in real-time.

3. An acoustic power control method as claimed in claim 1 further comprising the step of using system inputs representative of a present image to optimize acoustic output.

4. An acoustic power control method as claimed in claim 1 further comprising the step of combining the data with acoustic output levels and measurement database informa- 5. An acoustic power control method as claimed in claim 4 further comprising the step of computing modified gain levels by combining operator selected inputs with the acoustic output levels.

6. An acoustic power control method as claimed in claim 1 further comprising the steps of;

computing time constraint information using the measured database parameters; and optimally computing system transmit parameters using the measured database parameters.

7. An acoustic power control method as claimed in claim 1 wherein the system transmit parameters comprise transmit amplitude, transmit power supply control parameters and transmit burst length.

8. An acoustic power control method for optimizing acoustic power levels in an ultrasound imaging system having an operator control panel, the method comprising the steps of:

providing a measurement database containing measured database parameters;

optimally combining a current system imaging configuration with the measured database parameters to provide an optimal combination;

computing relevant system transmit parameters using the optimal combination to achieve optimization of transmit parameters;

providing accurate estimates of physical output data for computing output display indices; and adjusting the measured database parameters through the use of current scanning parameters to maximize system performance.

* * * * *